(12) United States Patent
Samaroo

(10) Patent No.: US 7,299,506 B1
(45) Date of Patent: Nov. 27, 2007

(54) BEDSORE PREVENTION KIT

(76) Inventor: Rohini Samaroo, 2818 Kensington Rd., Melbourne, FL (US) 32935

( * ) Notice: Subject to any disclaimer, the term of this patent is extended or adjusted under 35 U.S.C. 154(b) by 96 days.

(21) Appl. No.: 11/229,121

(22) Filed: Sep. 19, 2005

(51) Int. Cl.
*A41D 13/015* (2006.01)

(52) U.S. Cl. .............................. 2/455; 2/16; 2/20; 2/21; 2/22; 2/24

(58) Field of Classification Search .................. 2/16, 2/20, 21; 128/878, 879, 881, 882, 889, 892, 128/893, 894; 5/623, 624, 646, 648, 655.9, 5/499
See application file for complete search history.

(56) References Cited

U.S. PATENT DOCUMENTS

| | | | | |
|---|---|---|---|---|
| 2,077,202 A | * | 4/1937 | Barrie | 119/14.22 |
| 3,216,417 A | * | 11/1965 | Posey | 128/892 |
| 3,458,867 A | * | 8/1969 | Moore et al. | 2/16 |
| 3,496,573 A | * | 2/1970 | Pope et al. | 2/161.6 |
| 3,508,544 A | * | 4/1970 | Moore et al. | 128/892 |
| 3,648,291 A | | 3/1972 | Ponkers | |
| 3,831,467 A | * | 8/1974 | Moore | 602/26 |
| 5,123,113 A | | 6/1992 | Smith | |
| 5,364,339 A | | 11/1994 | Carver | |
| 5,462,519 A | | 10/1995 | Carver | |
| 5,472,413 A | * | 12/1995 | Detty | 602/26 |
| 5,700,173 A | * | 12/1997 | Lerro | 441/57 |
| 6,009,873 A | | 1/2000 | Neviaser | |
| D428,153 S | | 7/2000 | Davis | |
| 6,279,160 B1 | * | 8/2001 | Chen | 2/24 |
| 6,526,612 B1 | * | 3/2003 | Zarrella | 5/636 |
| 2002/0032485 A1 | * | 3/2002 | Flam et al. | 623/23.51 |

* cited by examiner

*Primary Examiner*—Katherine Moran
*Assistant Examiner*—Sally Colson Cline

(57) ABSTRACT

A bedsore prevention kit includes a finger grip that includes a tubular member having a first end and a second end. A strap is attached to and extends between the first and second ends. The strap is extendable over a plurality of fingers and the tubular member is positionable between the fingers and a palm of a hand. A palm protector has a first edge, a second edge, a third edge and a fourth edge. The first and second edges are positioned opposite of each other. The palm protector is wedge-shaped and has a decreasing thickness from the second edge to the first edge. The palm protector is positionable between a plurality of fingertips and the palm of a hand.

8 Claims, 4 Drawing Sheets

BEDSORE PREVENTION KIT

BACKGROUND OF THE INVENTION

1. Field of the Invention

The present invention relates to bedsore prevention devices and more particularly pertains to a new bedsore prevention device for the prevention of bedsores on the hands, toe area, heel, ankles, knee joints, and elbow joints of a person.

2. Description of the Prior Art

The use of bedsore prevention devices is known in the prior art. U.S. Pat. No. 5,123,113 describes a device for protecting selected body portions of a person from acquiring bedsores. Another type of bedsore prevention device is U.S. Pat. No. 3,648,291 which includes a garment that is positioned on a person to prevent bedsores. Yet another such device is found in U.S. Pat. No. 5,462,519 that includes a pad upon which a bedridden person may lay in order to prevent bedsores.

While these devices fulfill their respective, particular objectives and requirements, the need remains for a device for protecting particular areas of a body that are susceptible to sores, such as bedsores, from prolonged laying or sitting. In particular, the device should include protection for the palms of persons whose fingers are prone to being in a curled position. Additionally, knee joint and elbow joint protectors are needed for persons who are often sitting in a wheelchair.

SUMMARY OF THE INVENTION

The present invention meets the needs presented above by generally comprising a finger grip that includes a tubular member having a first end and a second end. A strap is attached to and extends between the first and second ends. The strap is extendable over a plurality of fingers and the tubular member is positionable between the fingers and a palm of a hand. A palm protector has a first edge, a second edge, a third edge and a fourth edge. The first and second edges are positioned opposite of each other. The palm protector is wedge-shaped and has a decreasing thickness from the second edge to the first edge. The palm protector is positionable between a plurality of fingertips and the palm of a hand There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
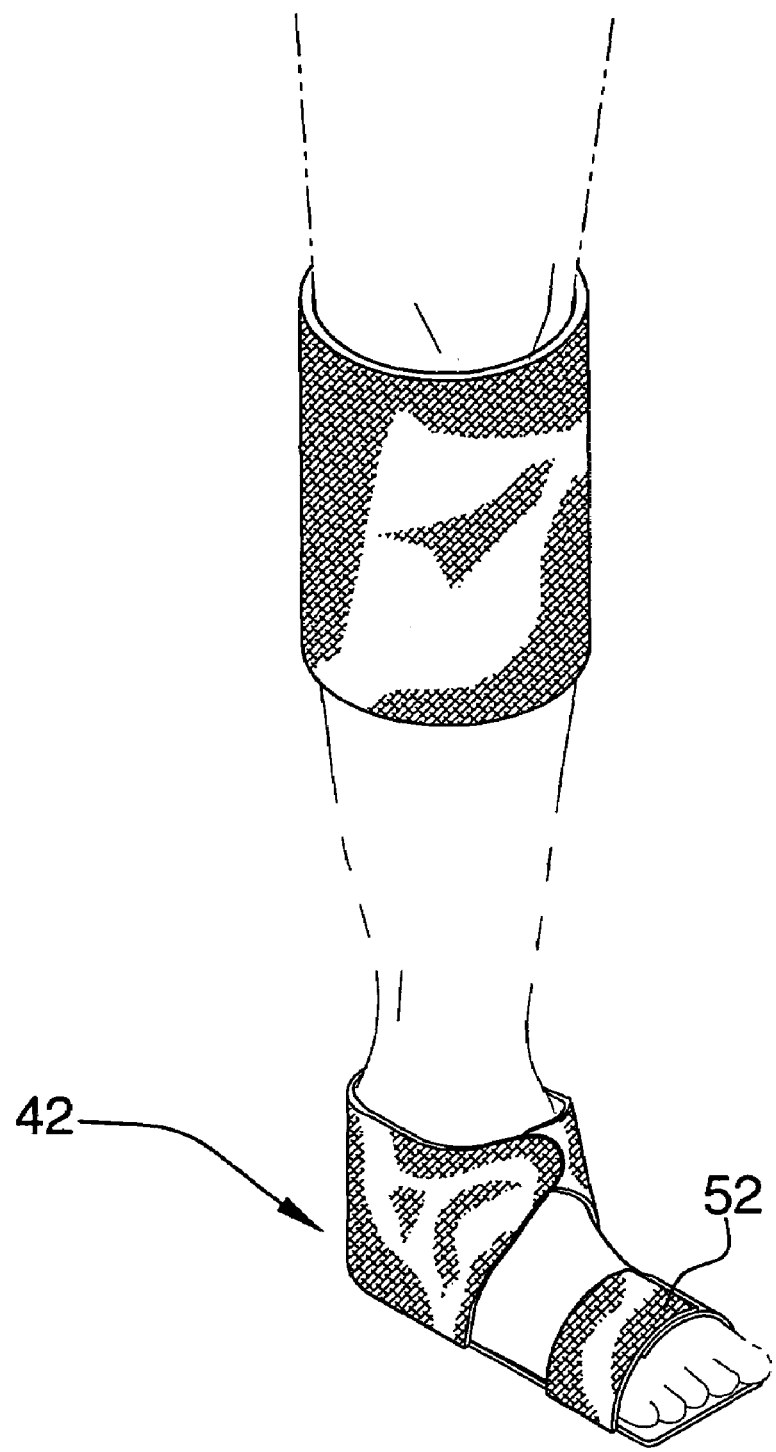
FIG. 1 is a perspective in-use view of foot and knee joint protectors of a bedsore prevention kit according to the present invention.
Figure 2:
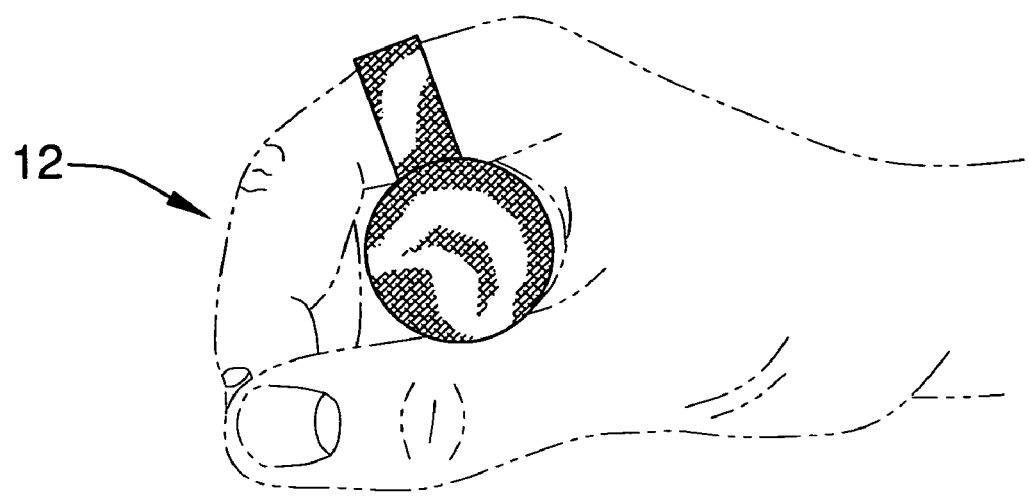
FIG. 2 is a side in-use view of a handgrip of the present invention.
Figure 3:
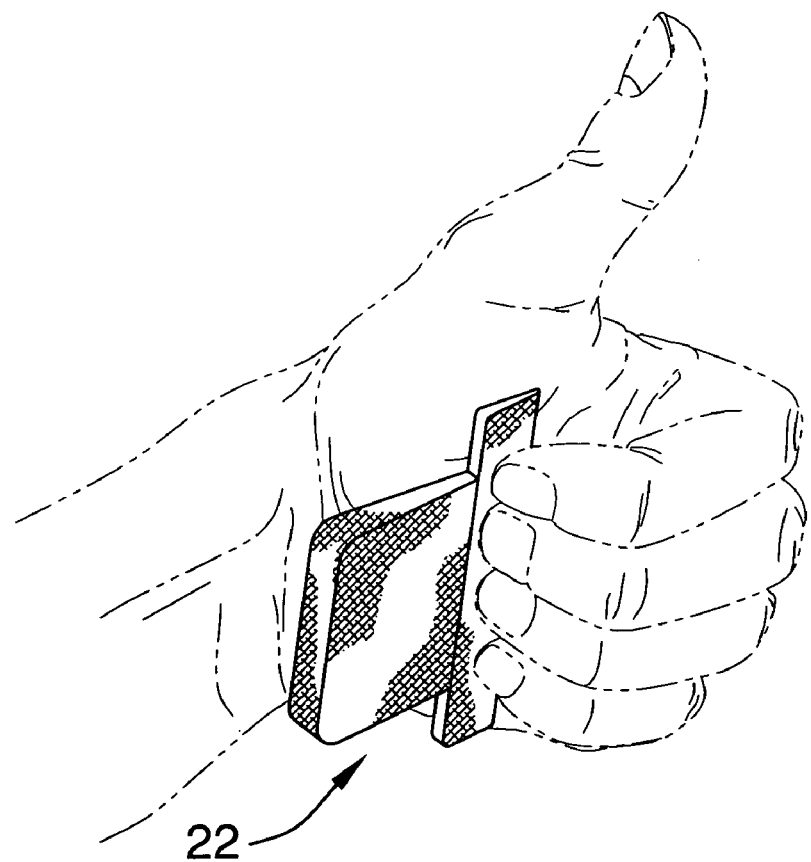
FIG. 3 is a perspective in-use view of a palm protector of the present invention.
Figure 4:
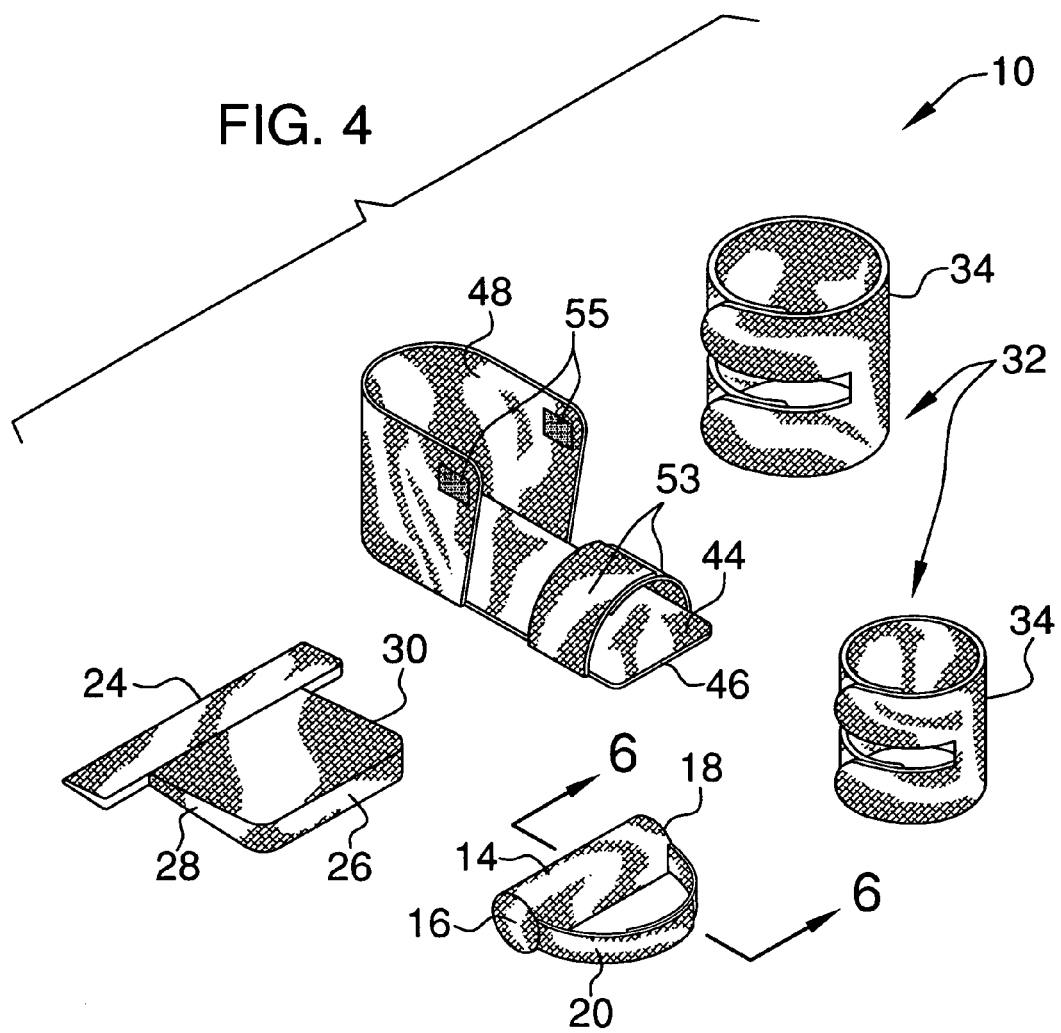
FIG. 4 is a perspective view of the present invention.
Figure 5:
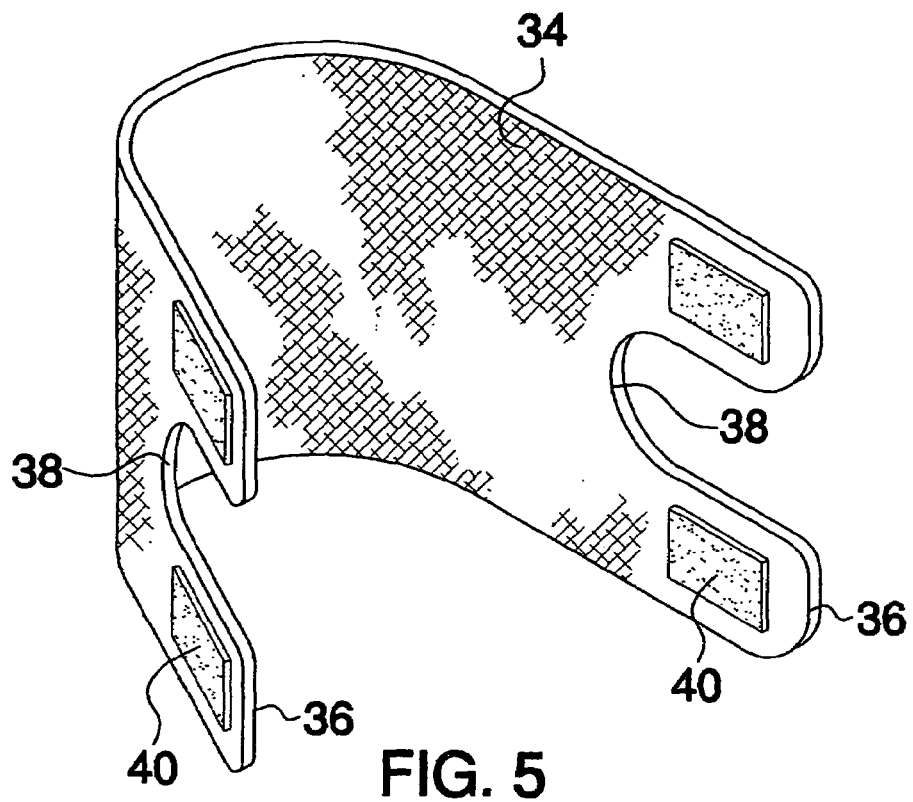
FIG. 5 is a perspective view of a joint covering of the present invention.
Figure 6:
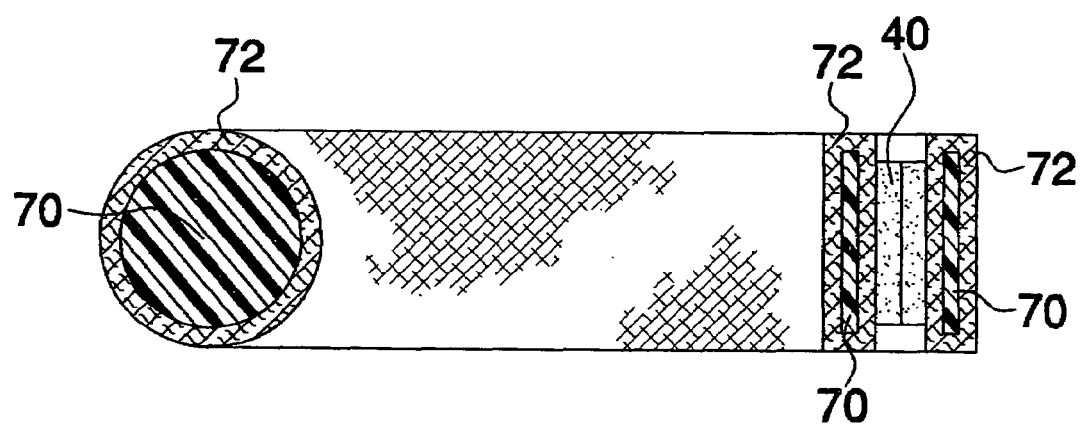
FIG. 6 is a cross-sectional view taken along line 6-6 of FIG. 4 of the present invention.

With reference now to the drawings, and in particular to FIGS. 1 through 6 thereof, a new bedsore prevention device embodying the principles and concepts of the present invention and generally designated by the reference numeral 10 will be described.

As best illustrated in FIGS. 1 through 6, the bedsore prevention kit 10 generally comprises a finger grip 12 including a tubular member 14 that has a first end 16 and a second end 18. A strap 20 is attached to and extends between the first 16 and second 18 ends. The strap 20 is extendable over a plurality of fingers and the tubular member 14 is positionable between the fingers and a palm of a hand to prevent the hand from locking into a fist position. The tubular member 14 and the strap 20 each include an interior comprising a resiliently compressible material 70 and outer layer comprising a flannel material 72. Strap 20 may include a pair of sections attached together by a hook and loop coupler 40.

A palm protector 22 has a first edge 24, a second edge 26, a third edge 28 and a fourth edge 30. The first 24 and second 26 edges are positioned opposite of each other. The palm protector 22 is wedge-shaped and has a decreasing thickness from the second edge 26 to the first edge 24. The palm protector 22 is positioned between a plurality of fingertips and the palm of a hand to prevent the fingertips from abutting the palm. The palm protector 22 includes an interior comprising a resiliently compressible material 70 and outer layer comprising a flannel material 72.

A plurality of knee and elbow joint coverings 32 is provided. Each of the knee and elbow joint coverings 32 includes a flexible panel 34 that has a pair of outer edges 36. Each of the outer edges 36 has a notch 38 extending therein. A hook and loop coupler 40 releasably couples the outer edges 36 together to define a loop. The notch 38 allows for flexibility in the loop. The knee and elbow joint coverings 32 may be selectively extended around knee or elbow joint and secured thereto with the hook and loop coupler 40. Each of the knee and elbow joint coverings 32 has an interior comprising a resiliently compressible material 70 and an outer layer comprising a flannel material 72.

A foot covering 42 includes a flexible base 44 that has a peripheral edge 46. A flexible rear wall 48 is attached to and extends upwardly from a portion of the peripheral edge 46 of the base 44. The rear wall 48 defines an ankle and heel covering. A coupler 52 is attached to the base 44 and is configured for removably attaching the base 44 to a foot and covering an ankle and heel with the ankle and heel covering. The coupler 52 includes a strap that is extendable over a foot adjacent to the toe. This coupler 52, aside from securing the foot covering 42 on a foot, also protects the first and fifth metatarsal and phalangeal joints. The strap may having a break therein and include a pair of straps 53 securable together with a conventional a hook and loop coupler. Further, a hook and loop coupler may 55 also be used for attaching together portions of the rear wall 48 as shown in FIG. 1. Each of the base 44 and rear wall 48 includes an interior comprising a resiliently compressible material 70 and outer layer comprising a flannel material 72. The resiliently compressible material 70 preferably includes a fleece material.

In use, the finger grip 12, palm protector 22, joint coverings 32 and foot covering 42 are used as indicated above and in the figures. These items prevent rubbing in areas where bedsores often occur.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A bed sore prevention system comprising:
a finger grip including a tubular member having a first end and a second end, a strap being attached to and extending between said first and second ends, said strap being extendable over a plurality of fingers and said tubular member being positionable between the fingers and a palm of a hand;
a palm protector having a first edge, a second edge, a third edge and a fourth edge, said first and second edges being positioned opposite of each other, said palm protector being wedge-shaped and having a decreasing thickness from said second edge to said first edge, said palm protector being positioned between a plurality of fingertips and the palm of a hand; and
a plurality of knee and elbow joint coverings, each of said knee and elbow joint coverings including a flexible panel having a pair of outer edges, each of said outer edges having a notch extending therein, a hook and loop coupler releasably coupling said outer edges together to define a loop, wherein said knee and elbow joint coverings may be selectively extended around knee or elbow joint and secured thereto with said hook and loop coupler.

2. The system according to claim 1, wherein said tubular member and said strap each includes an interior comprising a resiliently compressible material and outer layer comprising a flannel material, said palm protector including an interior comprising a resiliently compressible material and outer layer comprising a flannel material.

3. The system according to claim 2, further including a foot covering including a flexible base having a peripheral edge, a flexible rear wall being attached to and extending upwardly from a portion of said peripheral edge of said base, said rear wall defining an ankle and heel covering, a coupler being attached to said base and being configured for removably attaching said base to a foot and covering an ankle and heel with said rear wall, each of said base and said rear wall including an interior comprising a resiliently compressible material and outer layer comprising a flannel material.

4. The system according to claim 1, further including a foot covering including a flexible base having a peripheral edge, a flexible rear wall being attached to and extending upwardly from a portion of said peripheral edge of said base, said rear wall defining an ankle and heel covering, a coupler being attached to said base and being configured for removably attaching said base to a foot and covering an ankle and heel with said rear wall.

5. A bed sore prevention system comprising:
a finger grip including a tubular member having a first end and a second end, a strap being attached to and extending between said first and second ends, said strap being extendable over a plurality of fingers and said tubular member being positionable between the fingers and a palm of a hand, said tubular member and said strap each including an interior comprising a resiliently compressible material and outer layer comprising a flannel material;
a palm protector having a first edge, a second edge, a third edge and a fourth edge, said first and second edges being positioned opposite of each other, said palm protector being wedge-shaped and having a decreasing thickness from said second edge to said first edge, said palm protector being positioned between a plurality of fingertips and the palm of a hand, said palm protector including an interior comprising a resiliently compressible material and outer layer comprising a flannel material;
a plurality of knee and elbow joint coverings, each of said knee and elbow joint coverings including a flexible panel having a pair of outer edges, each of said outer edges having a notch extending therein, a hook and loop coupler releasably coupling said outer edges together to define a loop, wherein said knee and elbow joint coverings may be selectively extended around knee or elbow joint and secured thereto with said hook and loop coupler, each of said knee and elbow joint coverings having an interior comprising a resiliently compressible material and an outer layer comprising a flannel material; and
a foot covering including a flexible base having a peripheral edge, a flexible rear wall being attached to and extending upwardly from a portion of said peripheral edge of said base, said rear wall defining an ankle and heel covering, a coupler being attached to said base and being configured for removably attaching said base to a foot and covering an ankle and heel with said rear wall, said coupler being extendable over a foot and being positionable adjacent to toes attached to the foot, each of said base and said rear wall including an interior comprising a resiliently compressible material and outer layer comprising a flannel material.

6. A bed sore prevention system comprising:
a finger grip including a tubular member having a first end and a second end, a strap being attached to and extending between said first and second ends, said strap being extendable over a plurality of fingers and said tubular member being positionable between the fingers and a palm of a hand;
a palm protector having a first edge, a second edge, a third edge and a fourth edge, said first and second edges being positioned opposite of each other, said palm protector being wedge-shaped and having a decreasing thickness from said second edge to said first edge, said palm protector being positioned between a plurality of fingertips and the palm of a hand; and
a foot covering including a flexible base having a peripheral edge, a flexible rear wall being attached to and extending upwardly from a portion of said peripheral edge of said base, said rear wall defining an ankle and heel covering, a coupler being attached to said base and being configured for removably attaching said base to a foot and covering an ankle and heel with said rear wall.

7. The system according to claim 6, wherein said tubular member and said strap each includes an interior comprising a resiliently compressible material and outer layer comprising a flannel material, said palm protector including an interior comprising a resiliently compressible material and outer layer comprising a flannel material.

8. The system according to claim 7, further including a plurality of knee and elbow joint coverings, each of said knee and elbow joint coverings including a flexible panel having a pair of outer edges, each of said outer edges having a notch extending therein, a hook and loop coupler releasably coupling said outer edges together to define a loop, wherein said knee and elbow joint coverings may be selectively extended around knee or elbow joint and secured thereto with said hook and loop coupler, each of said knee and elbow joint coverings having an interior comprising a resiliently compressible material and an outer layer comprising a flannel material.

* * * * *